(12) United States Patent
Preuss et al.

(10) Patent No.: US 8,226,728 B2
(45) Date of Patent: Jul. 24, 2012

(54) INSERTION OF VIBRATION-DAMPING ELEMENTS IN PROSTHETIC SYSTEMS FOR THE MANIPULATION AND DAMPING OF NATURAL FREQUENCIES

(75) Inventors: Roman Preuss, Leinf.-Echterdingen (DE); Thomas Pandorf, Esslingen-Zell (DE); Patricie Merkert, Kirchheim u. Teck (DE)

(73) Assignee: CeramTec GmbH, Plochingen (DE)

( * ) Notice: Subject to any disclaimer, the term of this patent is extended or adjusted under 35 U.S.C. 154(b) by 159 days.

(21) Appl. No.: 12/375,711

(22) PCT Filed: Aug. 6, 2007

(86) PCT No.: PCT/EP2007/058124
§ 371 (c)(1),
(2), (4) Date: Jan. 30, 2009

(87) PCT Pub. No.: WO2008/015286
PCT Pub. Date: Feb. 7, 2008

(65) Prior Publication Data
US 2009/0326669 A1 Dec. 31, 2009

(30) Foreign Application Priority Data

Aug. 4, 2006 (DE) .......................... 10 2006 036 877
Jul. 6, 2007 (DE) .......................... 10 2007 031 667

(51) Int. Cl.
*A61F 2/42* (2006.01)
(52) U.S. Cl. .................................................. 623/22.14
(58) Field of Classification Search .... 623/21.11–21.19, 623/22.11, 23.11, 23.15, 23.39, 20.15, 22.3, 623/23.17, 23.21, 22.24–22.26, 22.45, 22.4, 22.41, 22.42, 22.14, 22.17–22.21
See application file for complete search history.

(56) References Cited

U.S. PATENT DOCUMENTS

| | | | | |
|---|---|---|---|---|
| 3,707,006 A | * | 12/1972 | Bokros et al. ................. | 424/422 |
| 3,795,922 A | * | 3/1974 | Herbert et al. ............. | 623/20.22 |
| 3,806,960 A | * | 4/1974 | Weber ........................ | 623/22.14 |
| 3,864,758 A | * | 2/1975 | Yakich ........................ | 623/22.13 |
| 3,894,297 A | * | 7/1975 | Mittelmeier et al. ....... | 623/22.14 |
| 4,129,903 A | * | 12/1978 | Huggler ..................... | 623/23.11 |

(Continued)

FOREIGN PATENT DOCUMENTS

DE    26 23 560    12/1976

(Continued)

OTHER PUBLICATIONS

International Search Report published on Feb. 7, 2008 in the corresponding international application No. PCT/US2007/058124

*Primary Examiner* — Alvin J. Stewart
(74) *Attorney, Agent, or Firm* — Fulbright & Jaworkski L.L.P.

(57) ABSTRACT

A hip joint prosthesis with a shaft fastened on the shaft head of which there is a ball head which in turn is inserted in a rotatable manner in the spherical recess of a socket insert and the socket insert is coupled with a hip socket wherein the shaft can be implanted in the femur and the hip socket can be implanted in the pelvic bone. To avoid transmission of vibrations, damping elements of a vibration-damping material are arranged at the coupling points of the shaft head with the ball head and/or of the socket insert with the hip socket.

13 Claims, 3 Drawing Sheets

U.S. PATENT DOCUMENTS

| | | | | |
|---|---|---|---|---|
| 4,159,544 | A * | 7/1979 | Termanini | 623/22.14 |
| RE31,865 | E * | 4/1985 | Roux | 623/22.29 |
| 4,714,477 | A * | 12/1987 | Fichera et al. | 623/22.19 |
| 4,778,474 | A * | 10/1988 | Homsy | 623/22.14 |
| 4,795,471 | A * | 1/1989 | Oh | 623/22.19 |
| 4,798,610 | A * | 1/1989 | Averill et al. | 623/22.2 |
| 4,813,961 | A * | 3/1989 | Sostegni | 623/23.39 |
| 4,822,369 | A * | 4/1989 | Oueveau et al. | 623/22.14 |
| 4,840,631 | A * | 6/1989 | Mathys | 623/22.14 |
| 4,908,033 | A * | 3/1990 | Frey et al. | 623/22.19 |
| 4,908,034 | A * | 3/1990 | Weightman et al. | 623/22.43 |
| 4,921,500 | A * | 5/1990 | Averill et al. | 623/22.45 |
| 4,936,855 | A * | 6/1990 | Sherman | 623/22.2 |
| 5,002,580 | A * | 3/1991 | Noble et al. | 623/23.23 |
| 5,015,257 | A * | 5/1991 | Crowninshield et al. | 623/22.45 |
| 5,062,853 | A * | 11/1991 | Forte | 623/22.2 |
| 5,066,304 | A * | 11/1991 | Crowninshield et al. | 623/22.45 |
| 5,080,678 | A * | 1/1992 | Spotorno et al. | 623/22.14 |
| 5,108,447 | A * | 4/1992 | Zeiler et al. | 623/22.14 |
| 5,156,624 | A * | 10/1992 | Barnes | 623/22.45 |
| 5,181,926 | A * | 1/1993 | Koch et al. | 623/22.14 |
| 5,222,984 | A * | 6/1993 | Forte | 623/22.18 |
| 5,362,311 | A * | 11/1994 | Amino et al. | 623/22.45 |
| 5,425,779 | A * | 6/1995 | Schlosser et al. | 623/22.2 |
| 5,549,693 | A * | 8/1996 | Roux et al. | 623/22.14 |
| 5,549,697 | A * | 8/1996 | Caldarise | 623/22.26 |
| 5,549,700 | A * | 8/1996 | Graham et al. | 623/22.14 |
| 5,593,445 | A * | 1/1997 | Waits | 623/23.42 |
| 5,658,345 | A * | 8/1997 | Willi | 623/22.26 |
| 5,735,905 | A * | 4/1998 | Parr | 623/23.11 |
| 5,755,807 | A * | 5/1998 | Anstaett et al. | 623/22.2 |
| 5,879,397 | A * | 3/1999 | Kalberer et al. | 623/22.25 |
| 5,989,294 | A * | 11/1999 | Marlow | 623/22.16 |
| 6,059,833 | A * | 5/2000 | Doets | 623/22.21 |
| 6,093,208 | A * | 7/2000 | Tian | 623/22.2 |
| 6,096,083 | A * | 8/2000 | Keller et al. | 623/22.11 |
| 6,152,961 | A * | 11/2000 | Ostiguy et al. | 623/22.28 |
| 6,206,929 | B1 * | 3/2001 | Ochoa et al. | 623/22.17 |
| 6,336,941 | B1 * | 1/2002 | Subba Rao et al. | 623/22.42 |
| 6,475,243 | B1 * | 11/2002 | Sheldon et al. | 623/22.28 |
| 6,517,583 | B1 * | 2/2003 | Pope et al. | 623/23.6 |
| 6,527,809 | B1 * | 3/2003 | Doursounian et al. | 623/22.28 |
| 6,547,824 | B1 * | 4/2003 | Price | 623/18.11 |
| 6,589,282 | B2 * | 7/2003 | Pearl | 623/19.14 |
| 6,607,560 | B1 * | 8/2003 | Pfaff et al. | 623/22.45 |
| 6,682,566 | B2 * | 1/2004 | Draenert | 623/22.24 |
| 6,682,567 | B1 * | 1/2004 | Schroeder | 623/22.24 |
| 6,706,071 | B1 * | 3/2004 | Wolter | 623/22.13 |
| 6,709,739 | B1 * | 3/2004 | Mullen et al. | 428/313.9 |
| 6,761,741 | B2 * | 7/2004 | Iesaka | 623/22.26 |
| 6,797,007 | B1 * | 9/2004 | Von Chamier et al. | 623/22.45 |
| 6,802,866 | B2 * | 10/2004 | Bunz | 623/22.14 |
| 6,811,569 | B1 * | 11/2004 | Afriat et al. | 623/22.32 |
| 6,875,238 | B1 * | 4/2005 | Price | 623/23.11 |
| 6,916,342 | B2 * | 7/2005 | Frederick et al. | 623/22.29 |
| 6,942,701 | B2 * | 9/2005 | Taylor | 623/22.14 |
| 6,986,792 | B2 * | 1/2006 | McLean et al. | 623/22.29 |
| 7,153,328 | B2 * | 12/2006 | Kim | 623/22.19 |
| 7,169,185 | B2 * | 1/2007 | Sidebotham | 623/22.21 |
| 7,179,296 | B2 * | 2/2007 | Dooney | 623/22.21 |
| 7,264,636 | B2 * | 9/2007 | Lewis et al. | 623/22.24 |
| 7,335,231 | B2 * | 2/2008 | McLean | 623/22.15 |
| 7,393,362 | B2 * | 7/2008 | Cruchet et al. | 623/22.18 |
| 7,597,715 | B2 * | 10/2009 | Brown et al. | 623/22.32 |
| 7,641,699 | B2 * | 1/2010 | Unger | 623/23.35 |
| 7,648,531 | B2 * | 1/2010 | Krehl | 623/20.32 |
| 7,780,739 | B2 * | 8/2010 | Lakin et al. | 623/22.17 |
| 7,794,504 | B2 * | 9/2010 | Case | 623/22.21 |
| 7,833,276 | B2 * | 11/2010 | Auxepaules et al. | 623/22.18 |
| 7,846,212 | B2 * | 12/2010 | Lewis et al. | 623/22.24 |
| 8,007,539 | B2 * | 8/2011 | Slone | 623/22.15 |
| 2001/0051831 | A1 * | 12/2001 | Subba Rao et al. | 623/22.42 |
| 2002/0161394 | A1 * | 10/2002 | Macoviak et al. | 606/200 |
| 2003/0055510 | A1 * | 3/2003 | Bunz | 623/22.14 |
| 2003/0065398 | A1 | 4/2003 | Cueille et al. | |
| 2003/0074077 | A1 * | 4/2003 | Taylor | 623/22.26 |
| 2003/0074083 | A1 * | 4/2003 | LeGros et al. | 623/23.35 |
| 2003/0105529 | A1 * | 6/2003 | Synder et al. | 623/22.24 |
| 2003/0114935 | A1 * | 6/2003 | Chan et al. | 623/22.21 |
| 2003/0120347 | A1 * | 6/2003 | Steinberg | 623/22.17 |
| 2003/0130740 | A1 * | 7/2003 | Stocks et al. | 623/22.17 |
| 2003/0153981 | A1 * | 8/2003 | Wang et al. | 623/22.21 |
| 2003/0171817 | A1 * | 9/2003 | Rambert et al. | 623/22.17 |
| 2003/0181987 | A1 * | 9/2003 | Muirhead-Allwood | 623/22.15 |
| 2003/0187512 | A1 * | 10/2003 | Frederick et al. | 623/22.2 |
| 2003/0229398 | A1 * | 12/2003 | Iesaka | 623/22.17 |
| 2004/0019380 | A1 * | 1/2004 | Baege et al. | 623/11.11 |
| 2004/0024460 | A1 * | 2/2004 | Ferree | 623/17.12 |
| 2004/0054418 | A1 * | 3/2004 | McLean et al. | 623/22.17 |
| 2004/0054421 | A1 * | 3/2004 | McLean | 623/23.11 |
| 2004/0078083 | A1 * | 4/2004 | Gibbs et al. | 623/22.17 |
| 2004/0122524 | A1 * | 6/2004 | Hunter et al. | 623/22.18 |
| 2004/0193282 | A1 * | 9/2004 | Hanes | 623/22.21 |
| 2004/0199257 | A1 * | 10/2004 | Dooney | 623/22.24 |
| 2004/0220674 | A1 * | 11/2004 | Pria | 623/19.12 |
| 2004/0225370 | A1 * | 11/2004 | Cruchet et al. | 623/22.18 |
| 2004/0267374 | A1 * | 12/2004 | Friedrichs | 623/22.15 |
| 2004/0267375 | A1 * | 12/2004 | Friedrichs | 623/22.18 |
| 2005/0004678 | A1 * | 1/2005 | Richards | 623/22.28 |
| 2005/0171614 | A1 * | 8/2005 | Bacon | 623/22.19 |
| 2005/0228503 | A1 * | 10/2005 | Gundolf | 623/22.21 |
| 2005/0261776 | A1 * | 11/2005 | Taylor | 623/22.17 |
| 2006/0009857 | A1 * | 1/2006 | Gibbs et al. | 623/23.4 |
| 2006/0167556 | A1 * | 7/2006 | Lazennec et al. | 623/22.24 |
| 2006/0190089 | A1 * | 8/2006 | Montoya et al. | 623/22.28 |
| 2006/0200247 | A1 * | 9/2006 | Charrois | 623/19.11 |
| 2006/0217814 | A1 * | 9/2006 | Lambert et al. | 623/22.17 |
| 2007/0191962 | A1 * | 8/2007 | Jones et al. | 623/22.32 |
| 2007/0208428 | A1 * | 9/2007 | Tepic et al. | 623/22.32 |
| 2007/0299534 | A1 * | 12/2007 | Lewis et al. | 623/22.24 |
| 2008/0058951 | A1 * | 3/2008 | Saladino et al. | 623/23.24 |
| 2009/0076619 | A1 * | 3/2009 | Grappiolo et al. | 623/22.4 |
| 2009/0287312 | A1 * | 11/2009 | Berger et al. | 623/22.29 |
| 2010/0262257 | A1 * | 10/2010 | Cruchet | 623/22.29 |

FOREIGN PATENT DOCUMENTS

| | | |
|---|---|---|
| DE | 30 02 443 | 8/1981 |
| DE | 92 09 584 | 11/1992 |
| DE | 42 20 462 | 11/1993 |
| DE | 199 04 436 | 8/2000 |
| EP | 0 066 092 | 12/1982 |
| EP | 0 444 382 | 9/1991 |
| EP | 1 293 179 | 2/2003 |
| FR | 2 266 491 | 10/1975 |
| FR | 2 621 814 | 4/1989 |
| GB | 1 504 055 | 3/1978 |
| GB | 2 069 338 | 8/1981 |

* cited by examiner

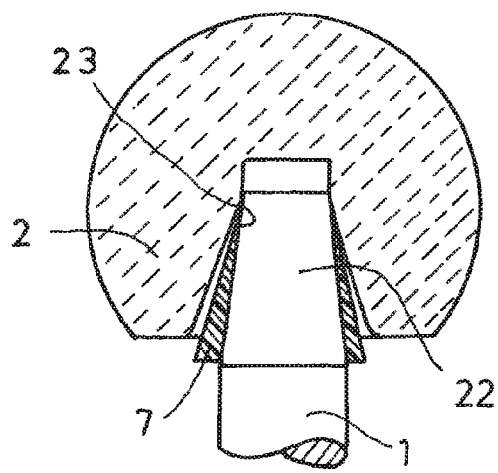
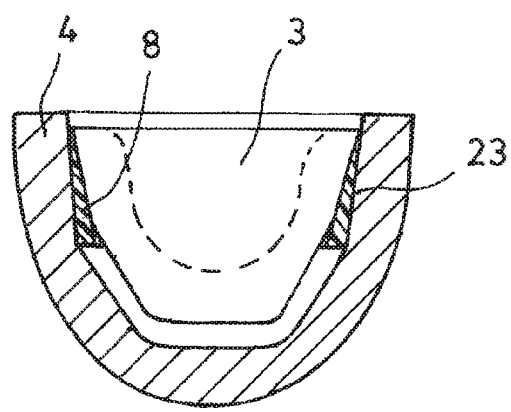
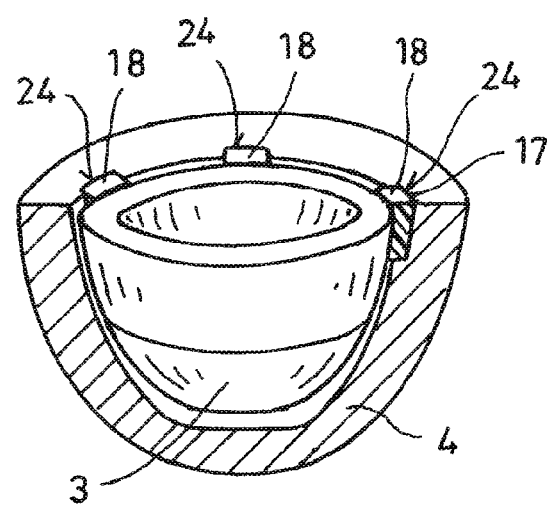

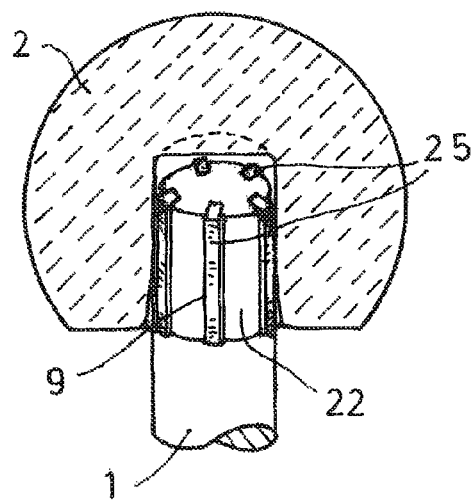
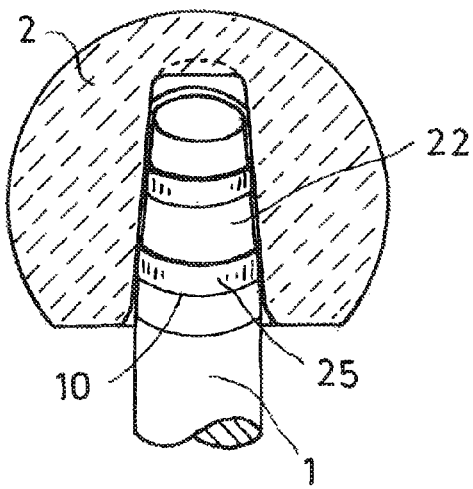
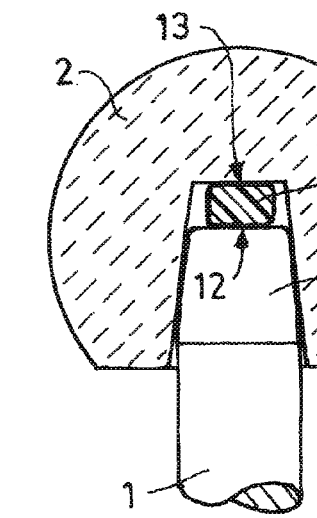
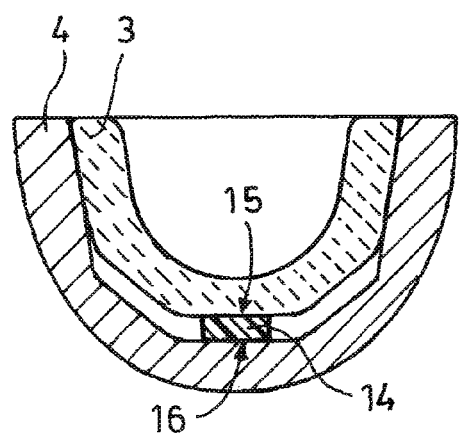

INSERTION OF VIBRATION-DAMPING
ELEMENTS IN PROSTHETIC SYSTEMS FOR
THE MANIPULATION AND DAMPING OF
NATURAL FREQUENCIES

CROSS-REFERENCE TO RELATED
APPLICATIONS

This application is a §371 of PCT/EP2007/058124 filed Aug. 6, 2007, which claims priority from DE 10 2006 036 877.0 filed Aug. 4, 2006 and DE 10 2007 031 667.6 filed Jul. 6, 2007.

BACKGROUND OF THE INVENTION

The invention relates to a hip-joint prosthesis having a shaft, fastened on whose shaft head there is a ball head which in turn is inserted in a rotatable manner in the hemispherical recess of a socket insert, and the socket insert is coupled with a hip socket, wherein the shaft can be implanted in the femur, and the hip socket can be implanted in the pelvic bone.

A plurality of prosthetic systems for replacing a natural hip joint exists on the market. As a rule, these consist of a shaft 1 coupled with a ball head 2 and of a hip socket 4 coupled with a socket insert 3. The shaft 1 and the hip socket 4 are connected to the body as a result of growing into the femur (20) and pelvic bone (21) respectively and are carriers for the ball head 2 and the socket insert 3 respectively. The ball head 2 is rotatably mounted in the hemispherical recess of the socket insert 3—degree of freedom: 1 (see FIG. 1).

During the articulation of the ball head in the hemispherical recess of the socket insert, for various reasons and in particular when materials of high levels of hardness are used for the ball head and socket insert (e.g. metal alloys, ceramic materials), undesirable solid-body friction can occur between the sliding partners. Depending on the material pairing, surface structure and relative speed of the two friction partners, during the movement under the effect of solid-body friction a so-called stick-slip effect can occur. This means that the quasi-continuous movement of the ball head in the hemispherical recess, when looked at closely, is made up of many temporally very short movement cycles—in each case a short movement directly followed by sudden stoppage and in turn sudden movement.

This stick-slip effect is caused by constant alternation of static and sliding friction.

The vibrations emitted in consequence of the occurrence of the stick-slip effect act as excitation and lead to the vibration of the individual components of the artificial joint. If one or more of the characteristic frequencies of the components then lies/lie in the audible spectrum (approximately 16-20000 Hz), it/they can be perceived acoustically by the patient as the carrier of the artificial hip-joint prosthesis, for example in the form of so-called squeaking. This is undesirable for the patient, is possibly also perceived in his surroundings and, if applicable, leads to a considerable personal restriction.

BRIEF SUMMARY OF THE INVENTION

The underlying object of the invention is to develop further a hip-joint prosthesis in accordance with the preamble of claim 1 in such a way that no squeaking occurs.

This object is achieved in that arranged at the coupling points of the shaft head with the ball head and/or of the socket insert with the hip socket there are damping elements consisting of a vibration-damping material. As a result of these damping elements a shift of the characteristic frequencies of the prosthetic system and a damping of the amplitudes that occur are brought about. The vibrations can be shifted into the non-audible range, or the acoustic phenomena occur with reduced sound pressure and thus in a less disturbing manner. The damping elements can then be provided both serially and in parallel in the vibratory prosthetic system.

Damping elements that are arranged serially in the vibratory system must be inserted at the coupling points between the individual components. An arrangement between the metal component (shaft, hip socket) and bone does not seem expedient in this case, since the bone as a body tissue already has very good damping properties. An arrangement in the sliding pairing likewise does not seem expedient, since the sliding pairing with its tribological properties is changed and the damping element would have to perform additional primary functions. Instead, an arrangement between the ball head and the shaft and/or between the hip socket and the socket insert is proposed.

In a development in accordance with the invention, the damping element is therefore an adapter sleeve that is arranged between the shaft head and the ball head.

In addition or alternatively, the damping element is an adapter ring that is arranged between the socket insert and the hip socket.

Damping elements that are arranged in parallel in the vibratory system are inserted close to the coupling points between the individual components. An arrangement between the metal components (shaft, hip socket) and the bone does not seem expedient in this case, since the bone as a body tissue already has very good damping properties. An arrangement in the sliding pairing is also ruled out. The damping elements are inserted close to the coupling points between the ball head and the shaft and/or between the hip socket and the socket insert.

In accordance with the invention, the damping elements are therefore formed as an adapter sleeve and/or as an adapter ring and have a wedge-shaped cross-section and are inserted close to the coupling points of the shaft head with the ball head and/or of the socket insert with the hip socket.

In the case of a coupling of the shaft head with the ball head and/or of the socket insert with the hip socket by means of a conical clamping, the damping elements in a development in accordance with the invention have a wedge-shaped cross-section and are pressed into the existing angled gaps of the instances of conical clamping. These damping elements, also referred to as adapter sleeves, can be pressed in a targeted manner into the existing angled gaps of the instances of conical clamping.

In the case of a coupling of the socket insert with the hip socket by means of a conical clamping, arranged in the hip socket at the upper cone end there are preferably recesses into which damping elements are pressed.

If precisely in the case of hip sockets recesses that are required for the engagement of positioning instruments or other instruments already exist at the upper cone end, these can also be used for the introduction of damping elements.

In this connection, the introduction of the damping elements is then possible, as desired, before or after the insertion of the socket insert. Even subsequent introduction is then conceivable in the course of a shaft-inspection.

In another development of the invention there are, introduced in the shaft head in the coupling faces coupling with the ball head, grooves in which damping elements are inserted. These grooves are preferably longitudinal or transverse grooves.

In another inventive development there is a damping element arranged between the end face of the prosthetic cone of the shaft head and the dome of the ball head.

In a manner equivalent to that of the ball head, in another development there is a damping element arranged between the base of the socket insert and the base of the hip socket.

The vibration-damping material is preferably a plastics material, such as PEEK, PE, PU, silicone or a porous material, such as a plastics foam or a metal foam. The abbreviations given stand for:

PEEK=polyether ether ketone
PE=polyethylene
PU=polyurethane.

BRIEF DESCRIPTION OF THE SEVERAL VIEWS OF THE DRAWING

FIG. 4 shows a ball bead 2 is set onto a shaft head 22 of a shaft 1.

FIG. 5 shows a socket insert 3 is inserted into a hip socket 4.

FIG. 6 shows a hip socket 4 with an inserted socket insert.

FIGS. 7 and 8 show the grooves which locate in the coupling faces of shaft head 22.

FIG. 9 shows a damping element 11, which is between the end face 12 of the prosthetic cone of the shaft head 22 and the dome 13 of the ball head 2.

FIG. 10 shows a damping element 14, which is between the base 15 of the socket insert 3 and the base 16 of the hip socket 4.

DETAILED DESCRIPTION OF THE INVENTION

The prior art and the invention are explained in greater detail in the following with the aid of figures.

Figure 1:
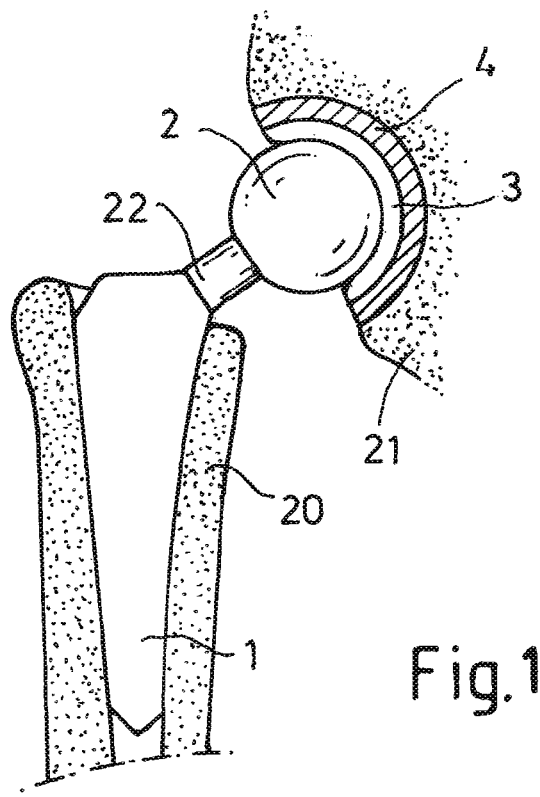
FIG. 1 shows a hip prosthesis in the prior art.

FIG. 1 shows the prior art. A hip prosthesis as a rule consists of a shaft 1 coupled with a ball head 2 and of a hip socket 4 coupled with a socket insert 3. The shaft 1 and the hip socket 4 are connected to the body of the patient as a result of growing into the femur 20 and the pelvic bone 21 respectively and are carriers for the ball head 2 and the socket insert 3 respectively. The ball head 2 is rotatably mounted in the hemispherical recess of the socket insert 3.

Figure 2:
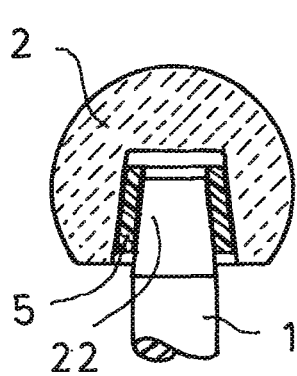
FIG. 2 shows a ball head 2 which is connected to the shaft head 22 of a shaft 1 by an adapter sleeve 5.

FIG. 2 shows a ball head 2 which is connected to the shaft head 22 of a shaft 1 by way of an adapter sleeve 5. The shaft head 22 is formed as a cone. In adaptation to this, the inside of the adapter sleeve 5 is also formed as a cone. Set on the outside of the adapter sleeve, likewise formed as a cone, is the ball head 2 with its inner cone face. In order to suppress the transmission of vibrations, the adapter sleeve is formed as a damping element made from a vibration-damping material. The vibration-damping material here is a plastics material, such as PEEK, PE, PU, silicone, or a porous material, such as a plastics foam or a metal foam.

Figure 3:
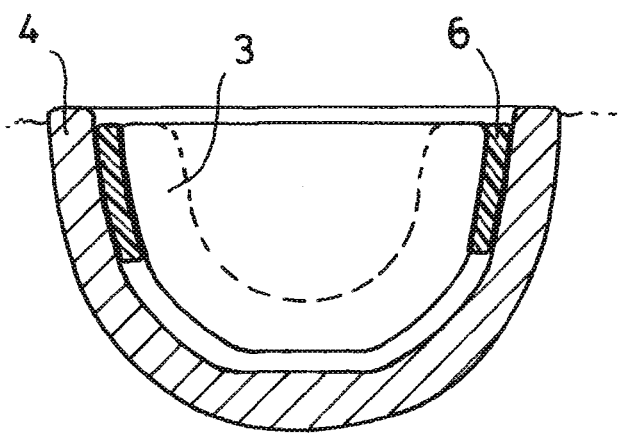
FIG. 3 shows a socket insert 3 is anchored into a hip socket 4 with an adapter ring 6 by means of a conical clamping.

FIG. 3 shows a hip socket 4 into which a socket insert 3 is anchored by means of a conical clamping by way of an adapter ring 6. The parts are coupled, in each case, by way of a conical clamping. In order to suppress the transmission of vibrations, here as well the adapter ring 6 is formed as a damping element made from a vibration-damping material.

Damping elements that are arranged in parallel in the vibratory system are shown in FIGS. 4, 5, 6. The damping elements are inserted close to the coupling points between the ball head 2 and the shaft head 22 and/or between the hip socket 4 and the socket insert 3.

FIG. 4 shows a shaft head 22 of a shaft 1, onto which a ball head 2 is set. The inner cone of the ball head 2 is formed differently, in terms of its angle, with respect to the cone of the shaft head 22 so that an angled gap 23 is formed, adjoining the coupling point of the ball head 2 and the shaft head 22. An adapter sleeve 7 with a wedge-shaped cross-section is pressed into this angled gap 23. In order to suppress the transmission of vibrations, here as well the adapter sleeve 7 is formed as a damping element made from a vibration-damping material.

FIG. 5 shows a hip socket 4 into which a socket insert 3 is inserted. In a similar manner to that of the angled gap 23 of FIG. 4, an adapter ring 8 with its wedge-shaped cross-section is pressed into the angled gap 23. In order to suppress the transmission of vibrations, here as well the adapter ring 8 is formed as a damping element made from a vibration-damping material.

The adapter sleeve 7 of FIG. 4 and the adapter ring 8 of FIG. 5 are thus pressed in a targeted manner into the existing angled gaps 23 of the instances of conical clamping.

A hip socket 4 with a socket insert inserted is shown in FIG. 6. At the upper cone end 17 the hip socket 4 is provided with recesses 24 that are required for the engagement of positioning instruments or other instruments. In order to suppress the transmission of vibrations, here as well damping elements 18 are pressed in.

Shaft heads 22 of shafts 1, which in the coupling faces coupling with the ball head 2 have grooves 9, 10 in which damping elements 25 are inserted, are shown in FIGS. 7 and 8. In the embodiment in accordance with FIG. 7, the grooves are longitudinal grooves 9, that is, they extend in the longitudinal direction of the shaft head . . . [damping] elements 25 protrude a little out of the grooves 9, 10 and are compressed when the ball head 2 is set onto the shaft head 22. These damping elements 25 also serve to suppress the transmission of vibrations.

In the embodiment in accordance with FIG. 9, in order to avoid the transmission of vibrations, there is a damping element 11 arranged between the end face 12 of the prosthetic cone of the shaft head 22 and the dome 13 of the ball head 2. In the embodiment in accordance with FIG. 10, in order to avoid the transmission of vibrations, there is a damping element 14 arranged between the base 15 of the socket insert 3 and the base 16 of the hip socket 4. Both damping elements 11, 14 are compressed when the ball head 2 is set onto the shaft head 22 or when the socket insert 3 is inserted into the hip socket 4.

All the damping elements consist of a vibration-damping material which is preferably a plastics material, such as PEEK, PE, PU, silicone, or a porous material, such as a plastics foam or a metal foam.

The invention claimed is:

1. A hip-joint prosthesis having a shaft, fastened on a shaft head, which couples to a hall head which in turn is inserted in a rotatable manner in the hemispherical recess of a socket insert, the socket insert being coupled with a hip socket, wherein the shaft can be implanted in the femur, and the hip socket can be implanted in the pelvic bone, wherein a damping elements are arranged at coupling points of the shaft head with the ball head or at the coupling points of the socket insert with the hip socket or both, wherein the damping elements comprise a vibration-damping material, and wherein the damping elements shift vibration frequencies of the prosthesis during the movement so that the vibration frequencies are shifted into a non-audible range or acoustic phenomena associated with the prosthesis movement have a reduced sound pressure.

2. A hip-joint prosthesis according to claim 1, wherein the damping elements are an adapter sleeve that is arranged between the shaft head and the ball head.

3. A hip-joint prosthesis according to claim 1, wherein the damping elements are an adapter ring that is arranged between the socket insert and the hip socket.

4. A hip-joint prosthesis according to claim 1, wherein the damping elements are inserted close to the coupling points of the shaft head with the ball head or the coupling points of the socket insert with the hip socket or both.

5. A hip-joint prosthesis according to claim 4, having a coupling of the shaft head with the ball head or of the socket insert with the hip socket or both by means of a conical clamping, wherein the damping elements are formed as an adapter sleeve and/or as an adapter ring and has a wedge-shaped cross-section and is pressed into the existing angled gaps of the instances of conical clamping.

6. A hip joint prosthesis according to claim 1 having a coupling of the socket insert with the hip socket by means of a conical clamping, wherein arranged in the hip socket at the upper cone end there are recesses into which the damping elements are pressed.

7. A hip joint prosthesis according to claim 1, wherein grooves are introduced in coupling faces of the shaft head, which couples with the ball head, and the damping elements are inserted in said grooves.

8. A hip-joint prosthesis according to claim 7, wherein the grooves are longitudinal grooves or transverse grooves.

9. A hip joint prosthesis according to claim 1, wherein the shaft head has a prosthetic cone with an end face, and the ball head has a dome, and a damping elements are arranged between the end face of the prosthetic cone of the shaft head and the dome of the ball head.

10. A hip joint prosthesis according to claim 1, wherein the damping elements are arranged between a base of the socket insert and a base of the hip socket.

11. A hip joint prosthesis according to claim 1, wherein the vibration-damping material is a plastic.

12. A hip-prosthesis according to claim 11, wherein the plastic is selected from the group consisting PEEK, PE, PU, silicone, or a porous material.

13. A hip-prosthesis according to claim 11, wherein the plastic is a plastic foam.

* * * * *